(12) United States Patent
Malanowska-Stega et al.

(10) Patent No.: US 11,364,020 B2
(45) Date of Patent: Jun. 21, 2022

(54) BRUSH BIOPSY DEVICE, KIT AND METHOD

(71) Applicants: Zanetta Malanowska-Stega, Southampton, NY (US); Damian Stega, Southampton, NY (US)

(72) Inventors: Zanetta Malanowska-Stega, Southampton, NY (US); Damian Stega, Southampton, NY (US)

(73) Assignee: Techmed Ventures, LLC, New York, NY (US)

( * ) Notice: Subject to any disclaimer, the term of this patent is extended or adjusted under 35 U.S.C. 154(b) by 819 days.

(21) Appl. No.: 15/838,153

(22) Filed: Dec. 11, 2017

(65) Prior Publication Data

US 2018/0161021 A1     Jun. 14, 2018

Related U.S. Application Data

(60) Provisional application No. 62/432,278, filed on Dec. 9, 2016.

(51) Int. Cl.
*A61B 10/02* (2006.01)
*A61B 10/04* (2006.01)

(52) U.S. Cl.
CPC .......... *A61B 10/02* (2013.01); *A61B 10/0283* (2013.01); *A61B 10/0291* (2013.01);
(Continued)

(58) Field of Classification Search
CPC ............ A61B 10/0216; A61B 10/0283; A61B 10/0291; A61B 10/02; A61B 10/04;
(Continued)

(56) References Cited

U.S. PATENT DOCUMENTS 1,835,122 A     5/1926  Desire
1,719,428 A     5/1927  William
(Continued)

FOREIGN PATENT DOCUMENTS

CA          1023632 A     6/1973
EP          0363196       4/1990
(Continued)

OTHER PUBLICATIONS

Feldman, Sarah, Ross S. Berkowitz, and Anna Na Tosteson. "Cost-effectiveness of strategies to evaluate postmenopausal bleeding." Obstetrics and gynecology 81, No. 6 (1993): 968-975.

(Continued)

*Primary Examiner* — Alex M Valvis
*Assistant Examiner* — Chanel J Jhin
(74) *Attorney, Agent, or Firm* — Hoffberg & Associates; Steven M. Hoffberg

(57) ABSTRACT

A biopsy device, comprising a flexible coaxial structure, comprising an obturator within a sheath, the obturator being adapted to be displaced with respect to the sheath along the coaxial axis by a force applied at a proximal end; a disruptor, at a distal end of the obturator, adapted to disrupt a tissue surface to free cells therefrom, having a first position covered within the sheath and a second position freely extending beyond the sheath; an element, having a fixed position on the sheath, configured to limit a depth of insertion of the sheath into a cervix.

20 Claims, 6 Drawing Sheets

(52) U.S. Cl.
CPC ...... *A61B 10/04* (2013.01); *A61B 2010/0208* (2013.01); *A61B 2010/0216* (2013.01); *A61B 2010/0225* (2013.01)

(58) Field of Classification Search
CPC .... A61B 2010/0208; A61B 2010/0216; A61B 2010/0225
USPC ........................................................ 600/569
See application file for complete search history.

(56) References Cited

U.S. PATENT DOCUMENTS

| | | | |
|---|---|---|---|
| 1,967,597 | A | 7/1932 | Rudolf |
| 2,360,051 | A | 7/1941 | Eweson |
| 2,495,794 | A | 12/1946 | Weller |
| 2,601,513 | A | 12/1948 | Gladstone |
| 2,623,521 | A | 3/1951 | Shaw |
| 2,701,559 | A | 8/1951 | Cooper |
| 2,763,104 | A | 7/1952 | Lindenberg |
| 2,739,585 | A | 6/1953 | Ernest |
| 2,839,049 | A | 3/1954 | Maclean |
| 2,955,591 | A | 5/1954 | Maclean |
| 2,729,210 | A | 6/1954 | Spencer |
| 2,767,703 | A | 1/1955 | Nieburgs |
| 2,881,756 | A | 2/1958 | Crosby et al. |
| 3,088,454 | A | 5/1963 | Shute |
| 3,196,876 | A | 7/1965 | Miller |
| 3,228,398 | A | 1/1966 | Leonard et al. |
| 3,308,825 | A | 3/1967 | Cruse |
| 3,400,708 | A | 9/1968 | Scheidt |
| 3,477,423 | A | 11/1969 | Griffith |
| 3,561,429 | A | 2/1971 | Jewett et al. |
| 3,587,560 | A | 6/1971 | Glassman |
| 3,613,662 | A | 10/1971 | Chrysostomides |
| 3,626,470 | A | 12/1971 | Antonides et al. |
| 3,656,472 | A | 4/1972 | Ben Moura |
| 3,776,219 | A | 12/1973 | Brown |
| 3,777,743 | A * | 12/1973 | Binard ............... A61B 10/0291 600/562 |
| 3,815,580 | A | 6/1974 | Oster |
| 3,838,681 | A | 10/1974 | Dalton |
| 3,877,464 | A | 4/1975 | Vermes |
| 3,881,464 | A | 5/1975 | Levene |
| 3,913,566 | A | 10/1975 | Lacey |
| 3,945,372 | A | 3/1976 | Milan et al. |
| 3,989,033 | A | 11/1976 | Halpern et al. |
| 3,995,619 | A | 12/1976 | Glatzer |
| 3,998,216 | A | 12/1976 | Hosono |
| 4,016,865 | A | 4/1977 | Fredricks |
| 4,023,559 | A | 5/1977 | Gaskell |
| 4,027,658 | A | 6/1977 | Marshall |
| 4,048,998 | A | 9/1977 | Nigro |
| 4,054,127 | A | 10/1977 | Milan et al. |
| 4,059,404 | A | 11/1977 | Schuster et al. |
| 4,108,162 | A | 8/1978 | Chikashige et al. |
| 4,127,113 | A | 11/1978 | Nollan |
| 4,136,680 | A | 1/1979 | Southworth |
| 4,177,797 | A | 12/1979 | Baylis et al. |
| 4,227,537 | A | 10/1980 | Suciu et al. |
| 4,235,244 | A | 11/1980 | Abele et al. |
| 4,239,040 | A | 12/1980 | Hosoya et al. |
| 4,256,119 | A | 3/1981 | Gauthier |
| 4,258,722 | A | 3/1981 | Sessions et al. |
| 4,262,676 | A | 4/1981 | Jamshidi |
| 4,266,555 | A | 5/1981 | Jamshidi |
| 4,318,414 | A | 3/1982 | Schuster et al. |
| 4,324,262 | A | 4/1982 | Hall |
| 4,340,066 | A | 7/1982 | Shah |
| 4,356,822 | A | 11/1982 | Winstead-Hall |
| 4,356,828 | A | 11/1982 | Jamshidi |
| 4,361,948 | A | 12/1982 | Omata |
| 4,403,617 | A | 9/1983 | Tretinyak |
| 4,448,205 | A | 5/1984 | Stenkvist |
| 4,465,072 | A | 8/1984 | Taheri |
| 4,485,824 | A | 12/1984 | Koll |
| 4,517,978 | A | 5/1985 | Levin et al. |
| 4,561,433 | A | 12/1985 | Wheeler et al. |
| 4,562,847 | A | 1/1986 | Nydahl et al. |
| 4,600,014 | A | 7/1986 | Beraha |
| 4,600,214 | A | 7/1986 | Spademan |
| 4,605,011 | A | 8/1986 | Naslund |
| 4,619,272 | A | 10/1986 | Zambelli |
| 4,620,548 | A | 11/1986 | Hasselbrack |
| 4,628,941 | A | 12/1986 | Kosasky |
| 4,641,663 | A | 2/1987 | Juhn |
| 4,662,381 | A | 5/1987 | Inaba |
| 4,667,684 | A | 5/1987 | Leigh |
| 4,699,154 | A | 10/1987 | Lindgren |
| 4,700,713 | A | 10/1987 | Kist |
| 4,726,373 | A | 2/1988 | Greengrass |
| 4,735,214 | A | 4/1988 | Berman |
| 4,747,414 | A | 5/1988 | Brossel |
| 4,754,764 | A | 7/1988 | Bayne |
| 4,759,376 | A | 7/1988 | Stormby |
| 4,762,133 | A | 8/1988 | Bayne et al. |
| 4,763,670 | A | 8/1988 | Manzo |
| 4,766,907 | A | 8/1988 | de Groot et al. |
| 4,766,908 | A | 8/1988 | Clement |
| 4,784,158 | A * | 11/1988 | Okimoto ............ A61B 1/00142 600/572 |
| 4,817,631 | A | 4/1989 | Schnepp-Pesch et al. |
| 4,873,992 | A | 10/1989 | Bayne |
| 4,877,037 | A | 10/1989 | Ko et al. |
| 4,919,146 | A | 4/1990 | Rhinehart et al. |
| 4,966,162 | A | 10/1990 | Wang |
| 4,981,143 | A | 1/1991 | Sakita et al. |
| 4,986,278 | A | 1/1991 | Ravid et al. |
| D316,488 | S | 4/1991 | Stormby |
| D317,361 | S | 6/1991 | Stormby |
| 5,022,408 | A | 6/1991 | Mohajer |
| 5,084,005 | A | 1/1992 | Kachigian |
| 5,131,402 | A | 7/1992 | Van Dooren |
| 5,133,361 | A | 7/1992 | Cox et al. |
| 5,146,928 | A | 9/1992 | Esser |
| 5,172,701 | A | 12/1992 | Leigh |
| 5,176,693 | A | 1/1993 | Pannek, Jr. |
| 5,184,626 | A | 2/1993 | Hicken |
| 5,191,899 | A | 3/1993 | Strickland et al. |
| 5,201,323 | A | 4/1993 | Vermeulen |
| D335,706 | S | 5/1993 | Mohajer |
| 5,217,023 | A | 6/1993 | Langdon |
| 5,217,024 | A | 6/1993 | Dorsey et al. |
| 5,253,652 | A | 10/1993 | Fast |
| 5,259,391 | A | 11/1993 | Altshuler et al. |
| 5,279,307 | A | 1/1994 | Mohajer |
| 5,348,022 | A | 9/1994 | Leigh et al. |
| 5,357,977 | A | 10/1994 | Michels |
| 5,370,128 | A | 12/1994 | Wainwright |
| 5,370,653 | A | 12/1994 | Cragg |
| 5,422,273 | A | 6/1995 | Garrison et al. |
| 5,427,115 | A | 6/1995 | Rowland et al. |
| 5,445,164 | A | 8/1995 | Worthen et al. |
| 5,456,265 | A | 10/1995 | Yim |
| 5,471,994 | A | 12/1995 | Guirguis |
| 5,476,104 | A | 12/1995 | Sheahon |
| 5,509,921 | A | 4/1996 | Karell |
| 5,533,517 | A | 7/1996 | Michels |
| 5,535,756 | A | 7/1996 | Parasher |
| 5,546,265 | A | 8/1996 | Santos et al. |
| 5,562,102 | A | 10/1996 | Taylor |
| 5,578,018 | A | 11/1996 | Rowland et al. |
| 5,623,941 | A | 4/1997 | Hedberg et al. |
| 5,713,368 | A | 2/1998 | Leigh |
| 5,713,369 | A | 2/1998 | Tao et al. |
| 5,722,423 | A | 3/1998 | Lind et al. |
| 5,738,109 | A | 4/1998 | Parasher |
| 5,787,891 | A | 8/1998 | Sak |
| 5,810,745 | A | 9/1998 | Chaffringeon |
| 5,817,032 | A | 10/1998 | Williamson, IV et al. |
| 5,823,954 | A | 10/1998 | Chaffringeon |
| 5,865,765 | A | 2/1999 | Mohajer |
| 5,899,850 | A | 5/1999 | Ouchi |
| 5,900,374 | A | 5/1999 | Otto-Nagels |
| 5,916,175 | A | 6/1999 | Bauer |

(56) References Cited

U.S. PATENT DOCUMENTS

| | | |
|---|---|---|
| 5,931,845 A | 8/1999 | Amyette |
| 5,954,670 A | 9/1999 | Baker |
| 6,013,036 A | 1/2000 | Caillouette |
| 6,030,397 A | 2/2000 | Monetti et al. |
| 6,036,658 A | 3/2000 | Leet et al. |
| 6,059,735 A | 5/2000 | Sgro |
| 6,066,102 A | 5/2000 | Townsend et al. |
| 6,099,539 A | 8/2000 | Howell et al. |
| 6,143,512 A | 11/2000 | Markovic et al. |
| 6,187,546 B1 | 2/2001 | ONeill et al. |
| 6,193,674 B1 | 2/2001 | Zwart |
| D441,141 S | 4/2001 | Shalita |
| 6,258,044 B1 | 7/2001 | Lonky et al. |
| 6,277,089 B1 | 8/2001 | Yoon |
| 6,336,905 B1 | 1/2002 | Colaianni |
| 6,346,086 B1 | 2/2002 | Maksem et al. |
| 6,352,513 B1 | 3/2002 | Anderson et al. |
| 6,387,058 B1 | 5/2002 | Wallach |
| 6,394,966 B1 | 5/2002 | Gill et al. |
| 6,409,681 B1 | 6/2002 | Caillouette |
| 6,494,845 B2 | 12/2002 | Rutenberg |
| 6,500,114 B1 | 12/2002 | Petitto et al. |
| 6,514,191 B1 | 2/2003 | Popowski et al. |
| 6,572,578 B1 | 6/2003 | Blanchard |
| 6,610,005 B1 | 8/2003 | Tao |
| 6,612,996 B2 | 9/2003 | Williams |
| 6,623,440 B1 | 9/2003 | Weldon |
| 6,638,504 B1 | 10/2003 | Lukanidin |
| 6,669,643 B1 | 12/2003 | Dubinsky |
| 6,676,609 B1 | 1/2004 | Rutenberg et al. |
| 6,723,057 B1 | 4/2004 | Pearce |
| 6,749,575 B2 | 6/2004 | Matriano et al. |
| D500,410 S | 1/2005 | Dragan |
| D500,553 S | 1/2005 | George |
| 6,926,677 B2 | 8/2005 | Richards |
| 6,947,788 B2 | 9/2005 | Gilboa et al. |
| 7,004,913 B1 | 2/2006 | Rutenberg et al. |
| 7,087,028 B2 | 8/2006 | Sak |
| 7,097,629 B2 | 8/2006 | Blair |
| 7,108,661 B2 | 9/2006 | Secrest et al. |
| 7,153,700 B1 | 12/2006 | Pardee et al. |
| 7,156,814 B1 | 1/2007 | Williamson, IV et al. |
| 7,207,951 B1 | 4/2007 | Lurie et al. |
| 7,214,229 B2 | 5/2007 | Mitchell et al. |
| 7,226,457 B2 | 6/2007 | Carson et al. |
| D561,333 S | 2/2008 | Zwart |
| 7,419,785 B2 | 9/2008 | Fuqua et al. |
| 7,429,650 B2 | 9/2008 | Fuqua et al. |
| D588,695 S | 3/2009 | Kim |
| 7,517,323 B2 | 4/2009 | Ng |
| 7,674,283 B2 | 3/2010 | Mitchell et al. |
| 7,741,433 B2 | 6/2010 | Pollock et al. |
| 7,749,173 B2 | 7/2010 | Larkin |
| 7,767,448 B2 | 8/2010 | Yong |
| 7,938,830 B2 | 5/2011 | Saadat et al. |
| 7,993,863 B2 | 8/2011 | Zetter et al. |
| 8,012,427 B2 | 9/2011 | Bommarito et al. |
| 8,052,613 B2 | 11/2011 | Assell et al. |
| 8,142,352 B2 | 3/2012 | Vivenzio et al. |
| 8,152,736 B2 | 4/2012 | Caillat et al. |
| 8,152,739 B1 | 4/2012 | McCully |
| 8,157,728 B2 | 4/2012 | Danna et al. |
| D658,388 S | 5/2012 | Persson |
| 8,178,317 B2 | 5/2012 | Roberts et al. |
| 8,221,480 B2 | 7/2012 | Boyden et al. |
| 8,251,918 B2 | 8/2012 | Larkin |
| 8,256,233 B2 | 9/2012 | Boyden et al. |
| 8,273,383 B2 | 9/2012 | Folkman et al. |
| 8,282,612 B1 | 10/2012 | Miller |
| 8,292,794 B2 | 10/2012 | Lubock et al. |
| 8,323,211 B2 | 12/2012 | Larkin |
| 8,328,710 B2 | 12/2012 | Lubock et al. |
| 8,343,733 B2 | 1/2013 | Gelvan et al. |
| 8,348,856 B1 | 1/2013 | Malanowska-Stega et al. |
| 8,361,095 B2 | 1/2013 | Osborne |
| 8,366,612 B2 | 2/2013 | Rosenthal |
| 8,376,958 B2 | 2/2013 | Larkin |
| 8,388,523 B2 | 3/2013 | Vivenzio et al. |
| 8,409,376 B2 | 4/2013 | Boyden et al. |
| 8,414,356 B2 | 4/2013 | Boyden et al. |
| 8,420,885 B2 | 4/2013 | Clarke et al. |
| 8,435,175 B2 | 5/2013 | McMahon et al. |
| 8,439,847 B2 | 5/2013 | Larkin |
| 8,452,068 B2 | 5/2013 | Averbuch et al. |
| 8,460,209 B2 | 6/2013 | Klein |
| 8,467,589 B2 | 6/2013 | Averbuch et al. |
| 8,473,032 B2 | 6/2013 | Averbuch |
| 8,485,861 B2 | 7/2013 | Boyden et al. |
| 8,517,956 B1 | 8/2013 | Malanowska-Stega et al. |
| 8,518,031 B2 | 8/2013 | Boyden et al. |
| D691,379 S | 10/2013 | Gunjian |
| D691,814 S | 10/2013 | Gonzalez-Gomez |
| 8,579,937 B2 | 11/2013 | Gresham |
| 8,604,172 B2 | 12/2013 | Sabbadini et al. |
| 8,617,144 B2 | 12/2013 | Ravikumar |
| 8,652,067 B2 | 2/2014 | Lonky et al. |
| D701,600 S | 3/2014 | Kauffman |
| 8,672,861 B2 | 3/2014 | Klein |
| 8,690,767 B2 | 4/2014 | Kecman |
| 8,697,139 B2 | 4/2014 | Phillips |
| 8,734,364 B1 | 5/2014 | Mantzaris et al. |
| 8,754,045 B2 | 6/2014 | Livingston |
| 8,762,067 B2 | 6/2014 | Boyden et al. |
| 8,784,384 B2 | 7/2014 | Boyden et al. |
| 8,784,385 B2 | 7/2014 | Boyden et al. |
| 8,788,211 B2 | 7/2014 | Boyden et al. |
| 8,795,197 B2 | 8/2014 | Lonky et al. |
| 8,798,932 B2 | 8/2014 | Boyden et al. |
| 8,798,933 B2 | 8/2014 | Boyden et al. |
| 8,801,628 B2 | 8/2014 | Teschendorf |
| 8,821,395 B2 | 9/2014 | McMahon et al. |
| 8,827,923 B2 | 9/2014 | Vom et al. |
| 8,849,441 B2 | 9/2014 | Boyden et al. |
| 8,858,912 B2 | 10/2014 | Boyden et al. |
| 8,920,336 B1 | 12/2014 | Malanowska-Stega et al. |
| 8,941,057 B2 | 1/2015 | Subramaniam |
| 8,968,213 B2 | 3/2015 | Roush et al. |
| 8,993,347 B2 | 3/2015 | Reisacher |
| 9,005,198 B2 | 4/2015 | Long et al. |
| 9,039,637 B2 | 5/2015 | Keady |
| 9,040,087 B2 | 5/2015 | Boyden et al. |
| 9,044,213 B1 | 6/2015 | Lonky |
| 9,050,070 B2 | 6/2015 | Boyden et al. |
| 9,050,251 B2 | 6/2015 | Boyden et al. |
| 9,050,317 B2 | 6/2015 | Boyden et al. |
| 9,056,047 B2 | 6/2015 | Boyden et al. |
| 9,060,926 B2 | 6/2015 | Boyden et al. |
| 9,060,931 B2 | 6/2015 | Boyden et al. |
| 9,060,934 B2 | 6/2015 | Boyden et al. |
| 9,072,688 B2 | 7/2015 | Boyden et al. |
| 9,072,799 B2 | 7/2015 | Boyden et al. |
| 9,078,642 B2 | 7/2015 | Vom et al. |
| 9,078,786 B1 | 7/2015 | Miller |
| 9,095,330 B2 | 8/2015 | Leahy et al. |
| 9,113,857 B2 | 8/2015 | Sethi |
| 9,117,258 B2 | 8/2015 | Averbuch |
| 9,119,604 B2 | 9/2015 | Gresham |
| 9,119,609 B2 | 9/2015 | OSullivan et al. |
| 9,173,779 B2 | 11/2015 | Triva |
| 9,271,803 B2 | 3/2016 | Averbuch et al. |
| 9,282,950 B2 | 3/2016 | Klein |
| 9,282,951 B2 | 3/2016 | Lonky et al. |
| 9,320,502 B2 | 4/2016 | OSullivan et al. |
| 9,332,898 B2 | 5/2016 | McMahon et al. |
| 9,351,712 B1 | 5/2016 | Malanowska-Stega et al. |
| 9,393,394 B2 | 7/2016 | Lonky et al. |
| 9,532,706 B2 | 1/2017 | McMahon et al. |
| 9,575,140 B2 | 2/2017 | Zur |
| 9,636,082 B2 | 5/2017 | Field |
| 9,642,591 B2 | 5/2017 | Field et al. |
| 9,655,600 B2 | 5/2017 | Lee-Sepsick |
| 9,659,374 B2 | 5/2017 | Averbuch |
| D790,225 S | 6/2017 | Poletto |
| 9,687,642 B2 | 6/2017 | Lonky et al. |

(56) References Cited

U.S. PATENT DOCUMENTS

| | | | |
|---|---|---|---|
| D790,863 S | 7/2017 | Poletto | |
| 9,707,002 B2 | 7/2017 | Henkes et al. | |
| 9,730,840 B2 | 8/2017 | Miller | |
| 9,743,904 B2 | 8/2017 | Field | |
| 9,750,483 B2 | 9/2017 | Weldon et al. | |
| 9,820,722 B1 | 11/2017 | Malanowska-Stega et al. | |
| 9,846,151 B2 | 12/2017 | Magniette | |
| 9,861,919 B2 | 1/2018 | Liddy et al. | |
| 9,883,792 B2 | 2/2018 | McMahon et al. | |
| 9,895,140 B1 | 2/2018 | Lonky | |
| 9,904,248 B2 | 2/2018 | Mathuis et al. | |
| 2002/0032389 A1 | 3/2002 | Fournier | |
| 2002/0068881 A1 | 6/2002 | Kobren et al. | |
| 2002/0161313 A1* | 10/2002 | Sak | A61B 10/0045 600/569 |
| 2002/0165467 A1 | 11/2002 | Rutenberg | |
| 2003/0036770 A1* | 2/2003 | Markman | A61F 2/10 606/187 |
| 2004/0015300 A1 | 1/2004 | Ganguli et al. | |
| 2004/0116827 A1 | 6/2004 | Fiberio | |
| 2004/0236247 A1 | 11/2004 | Rizvi | |
| 2005/0159721 A1 | 7/2005 | Yamamoto et al. | |
| 2005/0283129 A1 | 12/2005 | Hammons et al. | |
| 2006/0078882 A1 | 4/2006 | Zetter et al. | |
| 2006/0105343 A1 | 5/2006 | Zetter et al. | |
| 2006/0142668 A1 | 6/2006 | Friva | |
| 2006/0161076 A1 | 7/2006 | Gombrich et al. | |
| 2006/0241514 A1 | 10/2006 | Davies | |
| 2007/0073186 A1 | 3/2007 | Decker et al. | |
| 2007/0088248 A1 | 4/2007 | Glenn et al. | |
| 2007/0092891 A1 | 4/2007 | Willey et al. | |
| 2007/0092892 A1 | 4/2007 | Willey et al. | |
| 2007/0092893 A1 | 4/2007 | Willey et al. | |
| 2007/0231814 A1 | 10/2007 | Boman et al. | |
| 2008/0009764 A1 | 1/2008 | Davies | |
| 2008/0045924 A1 | 2/2008 | Cox et al. | |
| 2008/0154090 A1 | 6/2008 | Hashimshony | |
| 2008/0188769 A1 | 8/2008 | Lu | |
| 2010/0087845 A1 | 4/2010 | Spiro et al. | |
| 2010/0111837 A1 | 5/2010 | Boyden et al. | |
| 2010/0111846 A1 | 5/2010 | Boyden et al. | |
| 2010/0111847 A1 | 5/2010 | Boyden et al. | |
| 2010/0111848 A1 | 5/2010 | Boyden et al. | |
| 2010/0111849 A1 | 5/2010 | Boyden et al. | |
| 2010/0111850 A1 | 5/2010 | Boyden et al. | |
| 2010/0111854 A1 | 5/2010 | Boyden et al. | |
| 2010/0111855 A1 | 5/2010 | Boyden et al. | |
| 2010/0111938 A1 | 5/2010 | Boyden et al. | |
| 2010/0112067 A1 | 5/2010 | Boyden et al. | |
| 2010/0112068 A1 | 5/2010 | Boyden et al. | |
| 2010/0113614 A1 | 5/2010 | Boyden et al. | |
| 2010/0113615 A1 | 5/2010 | Boyden et al. | |
| 2010/0114348 A1 | 5/2010 | Boyden et al. | |
| 2010/0114547 A1 | 5/2010 | Boyden et al. | |
| 2010/0119557 A1 | 5/2010 | Boyden et al. | |
| 2010/0121466 A1 | 5/2010 | Boyden et al. | |
| 2010/0143243 A1 | 6/2010 | Boyden et al. | |
| 2010/0152651 A1 | 6/2010 | Boyden et al. | |
| 2010/0152880 A1 | 6/2010 | Boyden et al. | |
| 2010/0163576 A1 | 7/2010 | Boyden et al. | |
| 2010/0168900 A1 | 7/2010 | Boyden et al. | |
| 2010/0185174 A1 | 7/2010 | Boyden et al. | |
| 2010/0187728 A1 | 7/2010 | Boyden et al. | |
| 2010/0210968 A1 | 8/2010 | Lonky et al. | |
| 2011/0011190 A1 | 1/2011 | Subramaniam | |
| 2011/0077466 A1 | 3/2011 | Rosenthal | |
| 2011/0082358 A1 | 4/2011 | Davies | |
| 2011/0150765 A1 | 6/2011 | Boyden et al. | |
| 2011/0151477 A1 | 6/2011 | Reisacher | |
| 2011/0172557 A1 | 7/2011 | Lonky et al. | |
| 2011/0190659 A1 | 8/2011 | Long | |
| 2011/0201890 A1 | 8/2011 | Rosenthal | |
| 2012/0101738 A1 | 4/2012 | Boyden et al. | |
| 2012/0109015 A1 | 5/2012 | Kotmel et al. | |
| 2012/0109613 A1 | 5/2012 | Boyden et al. | |
| 2012/0115134 A1 | 5/2012 | Zetter et al. | |
| 2012/0122091 A1* | 5/2012 | Vom | A61B 90/06 435/6.11 |
| 2012/0128783 A1 | 5/2012 | Boyden et al. | |
| 2012/0289858 A1 | 11/2012 | Ouyang et al. | |
| 2013/0011332 A1 | 1/2013 | Boyden et al. | |
| 2013/0046316 A1 | 2/2013 | Sullivan et al. | |
| 2013/0158429 A1 | 6/2013 | Lee-Sepsick et al. | |
| 2013/0267870 A1 | 10/2013 | Lonky | |
| 2014/0128773 A1 | 5/2014 | Lonky et al. | |
| 2014/0163664 A1 | 6/2014 | Goldsmith | |
| 2014/0200511 A1 | 7/2014 | Boyden et al. | |
| 2014/0243705 A1 | 8/2014 | Lonky et al. | |
| 2015/0088032 A1 | 3/2015 | Lee-Sepsick | |
| 2015/0119795 A1 | 4/2015 | Germain et al. | |
| 2015/0133779 A1 | 5/2015 | Yurek et al. | |
| 2015/0157841 A1 | 6/2015 | Lonky et al. | |
| 2015/0185228 A1 | 7/2015 | Reisacher | |
| 2015/0272555 A1 | 10/2015 | Lonky | |
| 2016/0029960 A1 | 2/2016 | Toth et al. | |
| 2016/0033482 A1 | 2/2016 | Jolley et al. | |
| 2016/0103131 A1 | 4/2016 | Moses et al. | |
| 2016/0159918 A1 | 6/2016 | Pillai et al. | |
| 2016/0331357 A1* | 11/2016 | Czarnecki | A61B 10/04 |

FOREIGN PATENT DOCUMENTS

| | | |
|---|---|---|
| FR | 2305959 | 3/1976 |
| GB | 2159420 | 5/1985 |
| GB | 2208603 | 7/1987 |
| WO | WO9116855 | 5/1991 |
| WO | WO9301749 | 7/1992 |
| WO | WO9953841 | 4/1999 |

OTHER PUBLICATIONS

Dijkhuizen, F. Paul HLJ, Ben WJ Mol, Hans AM Brolmann, and A. Peter M. Heintz. "The accuracy of endometrial sampling in the diagnosis of patients with endometrial carcinoma and hyperplasia: a meta-analysis." Cancer 89, No. 8 (2000): 1765-1772.

Kohlberger, Petra D., Josefine Stani, Gerald Gitsch, Dirk G. Kieback, and Gerhard Breitenecker. "Comparative evaluation of seven cell collection devices for cervical smears." Acta cytologica 43, No. 6 (1999): 1023-1026.

Phillips, V., and W. G. McCluggage. "Results of a questionnaire regarding criteria for adequacy of endometrial biopsies." Journal of clinical pathology 58, No. 4 (2005): 417-419.

Huang, Gloria S., Juliana S. Gebb, Mark H. Einstein, Shohreh Shahabi, Akiva P. Novetsky, and Gary L. Goldberg. "Accuracy of preoperative endometrial sampling for the detection of high-grade endometrial tumors." American journal of obstetrics and gynecology 196, No. 3 (2007): 243-e1.

Tahir, M. M., M. A. Bigrigg, J. J. Browning, T. Brookes, and Phillip A. Smith. "A randomised controlled trial comparing transvaginal ultrasound, outpatient hysteroscopy and endometrial biopsy with inpatient hysteroscopy and curettage." BJOG: An International Journal of Obstetrics & Gynaecology 106, No. 12 (1999): 1259-1264.

Maim, Norzilawati M., Zaleha A. Mahdy, Shuhaila Ahmad, and Zainul Rashid M. Razi. "The Vabra aspirator versus the Pipelle device for outpatient endometrial sampling." Australian and New Zealand journal of obstetrics and gynaecology 47, No. 2 (2007): 132-136.

* cited by examiner

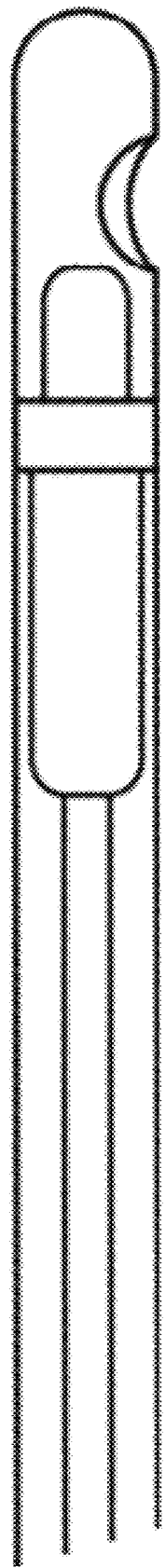
Fig. 4A (Prior Art)
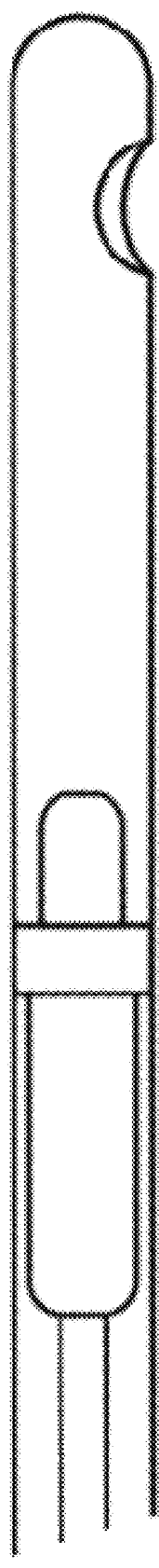
Fig. 4B (Prior Art)
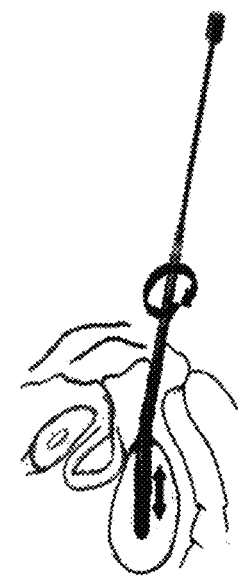
Fig. 5C (Prior Art)
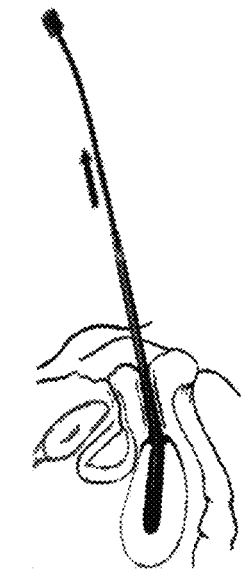
Fig. 5B (Prior Art)
Fig. 5A (Prior Art)

BRUSH BIOPSY DEVICE, KIT AND METHOD

CROSS REFERENCE TO RELATED APPLICATIONS

The present application is a non-provisional, and claims benefit of priority from U.S. Provisional Patent Application No. 62/432,278, filed Dec. 9, 2017, the entirety of which is expressly incorporated herein by reference.

FIELD OF THE INVENTION

The present invention provides a system and method for performing a biopsy of the uterus. More particularly, it is a device that disrupts and samples cells from the endometrium, and simultaneously takes a sample with an abrasive brush and an aspirate.

BACKGROUND OF THE INVENTION

The present technology represents improvements over U.S. Pat. Nos. 9,351,712, 8,920,336, 8,517,956, and 8,348,856, each of which are incorporated herein by reference in their entirety. Those patents, in turn, represent an improvement over the Cook Medical Tao Brush™ I.U.M.C. Endometrial Sampler, and the Pipelle endometrial biopsy device (See, Sierecki A R, Gudipudi D K, Montemarano N, Del Priore G., "Comparison of endometrial aspiration biopsy techniques: specimen adequacy." J Reprod Med. 53(10): 760-4, 2008 October), expressly incorporated herein by reference.

As shown in FIGS. 1A and 1B, the Tao Brush™ has a bead at the tip, to reduce trauma when the brush reaches the fundus of the uterus. FIG. 1A shows the brush extended from the sheath, while FIG. 1B shows the brush retracted. Proximal to the brush, on the guidewire, is an inner sleeve provided to center the wire, but this does not provide an interference fit, and does not draw a vacuum when the guidewire is retracted. The sample taken by the Tao Brush™ represents the cells swept or abraded from the endometrium, by the bristles. See also, U.S. Pat. Nos. 4,227,537, 3,877,464; 9,078,642; 5,916,175; 5,954,670; 6,059,735; 6,610,005; 7,767,448; 8,827,923; 8,439,847; 8,251,918; 7,749,173; 5,546,265; 3,881,464; 4,108,162; 8,968,213; 8,323,211; D658,388; 5,713,369; 5,546,265; 4,235,244; 4,754,764; 4,763,670; 4,966,162; 5,146,928; 5,253,652; 4,662,381; 5,217,024; 5,279,307; 6,336,905; each of which is expressly incorporated herein by reference in its entirety.

FIGS. 2A and 2B show a Tao Brush™, with the handle at the opposite end from the brush visible.

FIGS. 3A-3D show the use of the Tao Brush™. The manufacturer (Cook Medical) provides the following instructions for use:

1. Position screw-cap test tube containing 8 ml of CytoRich® Brush Cytology Preservative (AutoCyte, Inc., Elon College, NC) in a test-tube rack at the site of the procedure.
2. Place patient in lithotomy position.
3. Retract the brush sampler completely into the outer sheath. (FIG. 2)
4. Gently insert the device to the level of the fundus. (FIG. 3A)
5. Pull back the outer sheath all the way to the handle. Amply rotate the brush sampler. (FIG. 3B)

Two methods are suggested:
1) Rotate brush sampler in a clockwise manner until reference mark on the handle indicates completion of a 360° turn, then rotate counterclockwise the (opposite direction) until the reference mark on the handle indicates completion of a 360° turn;
2) Rotate the brush sampler in only one direction by completing 4 or 5 360° rotations. NOTE: Reference mark on handle indicates completion of a 360° rotation.

6. In order to trap endometrial material in situ, push the outer sheath over the brush to the tip and remove the device. (FIG. 3C). The normal endometrial cavity is in a collapsed state, so the brush will have direct contact with the entire endometrial surface.
7. Immediately immerse the device into 8 ml of CytoRich® Brush Cytology Preservative.
8. Retract the sheath to expose the brush to preservative solution.
9. Hold the sheath firmly and move the brush in and out of the sheath to clean it of adherent cells and tissue. (FIG. 3C) NOTE: Collections are stable in preservative for periods of up to several weeks.
10. Remove the brush assembly from the test-tube, replace the screw cap, and submit the tube to the laboratory for processing.

To Obtain Uncontaminated Endometrial Cultures
1. After insertion of a sterile, nonlubricated vaginal speculum, swab the ectocervix and the endocervical canal with povidone iodine solution. NOTE: Insert the swab about 1.5 cm into the endocervical canal to ensure adequate swabbing of the endocervix with the povidone.
2. Insert the brush into the endometrial cavity following steps 3-6 from the section preceding these instructions. The reference mark on the handle indicates completion of a 360° turn.
3. Remove sampler.
4. Wipe the rounded tip of the brush with 95% alcohol gauze.
5. Pull back the sheath. Prepare morphologic evaluation (if required) by preparing a direct smear on a sterile glass slide and spray-fix immediately.
6. For culture studies, place the brush into sterile Stuarts Transportation Medium and agitate for 5 seconds FIGS. 4A and 4B show a Pipelle biopsy tool, which aspirates a sample into a sheath, as shown in FIGS. 5A-5C, but does not have an exposed brush.

FIGS. 6-7 show the design according to U.S. Pat. Nos. 9,351,712, 8,920,336, 8,517,956, and 8,348,856, expressly incorporated herein by reference, which improve the Tao Brush™ design by implementing an aspiration biopsy in addition to an abrasive tissue sampling biopsy. This is achieved by providing an interference fitting plunger proximal to the biopsy brush, which draws in a fluid sample from the uterus as the brush is withdrawn into the sheath.

However, according to the Tao Brush™ design and that of U.S. Pat. Nos. 9,351,712, 8,920,336, 8,517,956, and 8,348,856, the brush is inserted either an arbitrary or estimated distance, or until resistance is encountered by the tip of the brush pushing against the fundus of the uterus, which risks unnecessary tissue damage, and in some cases, complications.

U.S. Pat. Nos. 9,351,712, 8,920,336, 8,517,956, and 8,348,856 discuss an intrauterine biopsy sampling device having a narrow cylindrical tube with a guidewire and biopsy sampling device at the end at the end of the guidewire, similar to a Cook Medical (Bloomington, Ind.) Tao Brush™ I.U.M.C. Endometrial Sampler, modified such that disposed within the sheath, is a piston-like structure which, when the wire is withdrawn through the sheath, draws a vacuum and sucks fluid surrounding the guidewire into the sheath. A vacuum biopsy sampling device, such as the known Pipelle endometrial suction curette produces a vacuum and draws it into the sheath by a similar principle, but lacks the brush or other biopsy sampling device at its distal end.

The device is a 1-3 mm diameter by 30-40 cm long coaxial "straw" 1 that can easily pass into the uterus endometrial cavity with little or no discomfort. It is malleable but rigid enough to apply sufficient force to pass through the cervix. In the center of the outer sheath, which is an impermeable tube, a thinner inner insert 2 can be extended beyond the end of the tube 3 into the uterus. Proximal from the biopsy brush is a suction element 4, which draws liquid into the sheath when the guidewire is withdrawn. The inner obturator disrupts the uterus to loosen and collect a biopsy sample of the uterus. The tissue sampling device includes a spirally twisted flexible wire with opposed proximal and distal ends. Also included is a plastic tube covering a significant portion of the wire to provide additional rigidity without making the overall brush stiff.

Along the distal end portion of the wire is a brush that includes bristles that were used for collecting a tissue sample. The bristles are fixed within the spirally twisted wire near the distal end and are tapered from smaller to larger towards the distal end of the wire. Tapering of the bristles from the distal end of the device allows for more global tissue collection of the endometrium because of the shape of the endometrial cavity. An atraumatic bulb is located on the extreme distal end of the twisted wire. The plastic tube and twisted wire are contained within a sheath of shorter length than the twisted wire, such that the sheath can be moved along the plastic tube to the atraumatic bulb on the distal end of the twisted wire, thereby covering the brush during insertion and removal after tissue collection.

Before insertion, the sheath can be moved into position over the distal end of the twisted wire to protect the brush during insertion. Having the brush covered during insertion also increases comfort for the patient and protects the brush from collecting tissue from unintended areas. The sheath is moved back toward the proximal end of the twisted wire after the device has been inserted to the proper collection depth, exposing the brush and allowing for collection of a tissue sample. The sheath may be moved to completely uncover the brush or may be moved in gradients to uncover portions of the brush. This allows the practitioner to adjust the effective collection area of the brush based on the anatomy of the patient.

The plastic tube covering the wire is scored in centimeter gradations along the plastic tube with markings indicating the exact length of the brush inserted into the uterus, starting from the distal tip of the brush to the proximal end of the plastic tube. This allows the clinician to know how deeply the brush is inserted into the uterus. The sheath is approximately the same length as the plastic tube and in position to cover the brush bristles prior to insertion. The sheath may be formed of a clear material such that the gradations on the plastic tube may be viewed through the sheath. The ability to measure insertion depth increases the certainty that the tissue sample collected is from the correct area. After a tissue sample is collected from the proper area, while the tissue sampling device remains inserted, the sheath can be moved back along the distal end of the twisted wire to cover the brush bristles before removing the brush. This allows for the tissue sample to be protected on the brush within the sheath during removal.

Additionally, the gradations along the flexible tube allow the practitioner to measure the length of bristles exposed. As the practitioner pulls the sheath from its insertion position towards the handle, the further the sheath is pulled the more bristles are exposed. The gradations (ruler) provide a visual confirmation of this measurement and allow the practitioner to be precise in exposing only a certain length of the brush bristles. This measurement allows the practitioner to have better control of where the tissue is sampled and allows the practitioner to adjust the length of brush based on patient specific parameters; such as uterine size measured during previous tests or inferred based on patient history. Control of brush exposure increases sampling precision and patient comfort.

Simultaneously with withdrawal of the inner obturator back into the narrow cylindrical tube, the device creates a weak suction to collect the disrupted sample into the outer tube. The entire apparatus is then withdrawn from the uterus and the sample is collected by reversing the process outside the body.

Combining two or more biopsy methods into one device, eliminates pain, discomfort, and inconvenience, e.g., a second procedure to obtain an adequate and accurate specimen. The multiple methods of specimen collection, e.g., disruption by physical means, and suction, used together, allows a gentler application of the individual methods, e.g. a gentle disruption and gentle suction applied simultaneously can replace a vigorous disruption, e.g. D&C, and a powerful suction. The combination of multiple gentler methods in one device is safer and more effective than any method alone.

See (each of which is expressly incorporated here by reference in its entirety):

Yang G C, Wan L S, Del Priore G. Factors influencing the detection of uterine cancer by suction curettage and endometrial brushing. J Reprod Med 2002; 47:1005-10.

Ries L A G, Melbert D, Krapcho M, Mariotto A, Miller B A, Feuer E J, Clegg L, Horner M J, Howlader N, Eisner M P, Reichman M, Edwards B K (eds). SEER Cancer Statistics Review, 1975-2004, National Cancer Institute. Bethesda, Md., seer.cancer.gov/csr/1975_2004/, based on November 2006 SEER data submission, posted to the SEER web site, 2007.

McCluggage W G. My approach to the interpretation of endometrial biopsies and curettings. J Clin Pathol. 2006; 59:801-12.

Dijkhuizen F P, Mol B W, Brolmann H A, Heintz A P. The accuracy of endometrial sampling in the diagnosis of the patients with endometrial carcinoma and hyperplasia: a meta-analysis. Cancer 2000; 89(8):1765-72.

Feldman S, Berkowitz R S, Tosteson A N. Cost-effectiveness of strategies to evaluate postmenopausal bleeding. Obstet Gynecol 1993; 81(6):968-75.

Grimes D A. Diagnostic dilation and curettage: A reappraisal. Am J Obstet Gynecol 1982; 142:1-6.

Ong S, Duffy T, Lenehan P, Murphy J. Endometrial pipelle biopsy compared o conventional dilatation and curettage. Jr J Med Sci 1997; 166:47-9.

Tahir M M, Bigrigg M A, Browning J J, Brookes S T, Smith P A. A randomized controlled trial comparing transvaginal ultrasound, outpatient hysteroscopy and endometrial biopsy with inpatient hysteroscopy and curettage. Br J Obstet Gynecol 1999; 106(12):1259-64.

Ferry J, Farnsworth A, Webster M, Wren B. The efficacy of the pipelle endometrial biopsy in detecting endometrial carcinoma. Aust N Z J Obstet Gynecol 1993; 33:1-76.

Guido R S, Kanbour-Shakir A, Rulin M, Christopherson W A. Pipelle endometrial sampling: sensitivity in the detection of endometrial cancer. J Reprod Med 1995; 40:553-5.

Stovall T G, Photopulos G J, Poston W M, Ling F W, Sandles L G. Pipelle endometrial sampling in patients with known endometrial carcinoma. Obstet Gynecol 1991; 77:954-6.

Van den Bosch T, Vandendael A, Wranz P A, Lombard C J. Endopap-versus Pipelle-sampling in the diagnosis of postmenopausal endometrial disease. Eur J Obstet Gynecol Reprod Biol 1996; 64:91-4.

Huang G S, Gebb J S, Einstein M H, et al. Accuracy of preoperative endometrial sampling for the detection of high-grade endometrial tumors. Am J Obstet Gynecol 2007; 196:243.e1-243.e5.

Kozuka T. Patch testing to exclude allergic contact dermatitis caused by povidone-iodine. Dermatology 2002; 204 Suppl 1:96-8.

Borja J M, Galindo P A, Gomez E, Feo F. Contact dermatitis due to povidone-iodine: allergic or irritant?. J Investig Allergol Clin Immunol 2003; 13(2):131-2.

Naim N M, Mandy Z A, Ahmad S, Razi Z R M. The Vabra aspirator versus the pipelle device for outpatient endometrial sampling. Aust N Z J Obstet Gynecol 2007; 47(2):132-6.

Phillips V, McCluggage W G. Results of a questionnaire regarding criteria for adequacy of endometrial biopsies. J Clin Pathol. 2005; 58:417-9.

SUMMARY OF THE INVENTION

A preferred embodiment of the present invention provides a narrow cylindrical tube with a guidewire and biopsy sampling device at the end, similar to a Cook Medical (Bloomington, Ind.) Tao Brush™ I.U.M.C. Endometrial Sampler, modified such that surrounding the cylindrical tube, a cervical stop is provided that limits insertion of the tube to a fixed distance past the external os of the uterus.

This feature may be combined with a suction device to draw a liquid sample in to the lumen of the narrow cylindrical tube, per U.S. Pat. Nos. 9,351,712, 8,920,336, 8,517,956, and 8,348,856.

The device is intended to collect tissue samples from the lining of the uterus (endometrium). The device has a brush at the distal end of the catheter. The brush is intended to gently sample the endometrium. The proximal end of the device has a handle for ease of physician handling. The device has a relatively rigid, outer sheath, that can be move along the length of the device (with respect to the handle), to cover or expose the brush at the distal end.

The device has a skirt stopper around the distal end of the outer sheath. The skirt is intended to locate the device in relation to the cervix, and may be fixed in position or manually slidable along the outer sheath (with a sufficiently tight fit to remain axially fixed in position after placement, such that when abutting the cervix, manipulation of the guidewire and the sheath will not reposition the skirt stopper). A series of axial markings are preferably provided to allow quantitative alignment of the skirt stopper along the sheath. The skirt stopper is preferably made of an elastomer with rounded edges, such as rubber, silicone, or plastic, having sufficient elasticity to provide the desired characteristics and avoid unintended traumatic injury.

The device is intended to be advanced into the patient with the brush covered by the outer sheath until the skirt encounters the cervix and can advance no further. After the skirt is stopped against the cervix, the brush is advanced past the end of the sheath by moving the guidewire with respect to the sheath, to expose the brush inside the uterus, to allow tissue sampling.

The device also has an O-ring secured to the main shaft of the catheter. The outer sheath and O-ring create a seal against each other, and create suction (vacuum) at the distal end of the catheter for securing tissue samples when the guidewire and brush are withdrawn into the sheath.

The device is removed from the patient with the brush covered by the outer sheath. An atraumatic bulb may be provided at the end of the brush, which can seal against the distal end of the sheath when the guidewire is withdrawn into the sheath. A stop may be provided to limit withdrawal of the guidewire into the sheath. For example, a toroidal or cylindrical member attached in fixed position inside the sheath may interfere with the O-ring, and thus limit retraction.

The device preferably sterile, and intended for single-use only.

In accordance with another embodiment of the invention, a multiple sample biopsy device is provided, capable of obtaining and segregating a plurality of biopsy samples taken in a single session. In accordance with this embodiment, the biopsy instrument is placed at an anatomical orifice, such as a cervical os or anus. Advantageously, a protrusion provides a positional reference with respect to the outer portion of the orifice, similar to the aforementioned skirt. This protrusion may be part of the design, or an added element to achieve the desired depth-of-insertion reference function.

The biopsy device according to this embodiment provides a plurality of biopsy sampling tools, which may each be the same or different, e.g., an endocervical sampler, an endometrial sampler, a punch sampler, and an endometrial sampler with suction. Each tool is provided as a device inside a sheath, such as a 1.5-4 mm tube, which is operable by a guidewire to extend the tool sampling head beyond the end of the sheath, twist with respect to the sheath, and retract the tool sampling head back within the sheath.

In addition to providing control over advancing the biopsy tool with respect to the sheath, each sheath is controllable to be selectively inserted into the orifice, and advance into the organ with the biopsy tool retracted into the sheath, and to be removed from the organ with the biopsy tool retracted into the sheath.

In some cases, the sheath itself may be articulable or angularly guidable to direct the biopsy tool to a desired region. The articulable sheath may be a single axis, i.e., a curvature of the end of the sheath, typically as a result of a tension on a tensile element such as cable, guidewire or filament attached to the wall of the sheath. By controlling the angle of curvature, and the rotational angle of the sheath with respect to the organ, a reasonable range of control is provided.

Similarly, a punch, or snare, or encapsulating biopsy device may also be controlled by a tension, which may be a wire or polymer filament. Thus, the case of a single guidewire with a single degree of freedom (advance/retract) is a simplest case, and additional controls and degrees of freedom may be provided.

In some cases, "blind" sampling may be accomplished, for example within a short canal, or at a distal portion of the organ with respect to the orifice.

In other cases, e.g., within a lumen of a larger organ, some imaging guidance is preferred. Therefore, the device may be used with an endoscope, and/or include an endoscopic camera, such as a 1-3 mm endoscopic camera. Typically, such devices rely on fiber optics from the tip to the imager, for both illumination and imaging. However, according to one embodiment of the technology, the imager circuit and lens are present at the tip of the scope, which in turn is disposed proximate to the end of the biopsy sampling device, to provide direct and real-time imaging of the biopsy procedure.

For example, On Semiconductor provides various suitable devices, such as the MT9V115 $\frac{1}{13}$" VGA, OV6922$\frac{1}{18}$" $\frac{1}{4}$ VGA imager, and OVM6946$\frac{1}{18}$" 400×400 imager, which may be included as part of a subminiature module that transmits the image as a data stream over an electrical interconnection (or wirelessly). The imager is typically provided with a field of view facing the biopsy tool, with a set of LEDs, or LED illuminated fibers, illuminating the field. While the camera is not required in all modes of operation, i.e., all sampling procedures, if provided, it may remain inserted into the orifice throughout the procedure. The camera may be present near the end of the sheath and advanced with the respective sheath of the biopsy tool into the organ during the procedure.

Advantageously, the video signal from the imager may be carried using the guidewire(s) which control the biopsy tool as electrical power and/or signal carriers. Note that the operating voltage is typically low, e.g., <3.3V, so a dangerous condition for the patient would not be present in case of electrical leakage. However, the power carrying members may be insulated to further reduce risk and enhance signal integrity. A wireless transmission may also be provided, for example to a nearby wireless receiver, avoiding the need for wired transmission. In that case, the device may have a self-contained battery, or receive operating power over a conductor which advantageously may include the guidewire. Since the preferred guidewire is multi-stranded, power and ground, and even signal, may be transmitted if the strands are mutually insulated. There is no compelling reason why a guidewire needs to be uninsulated, so this permits enhanced use of an existing structure, at low added cost and complexity.

The biopsy device according to this embodiment provides a barrel cartridge with the various biopsy tools in angularly displaced positions. One was to selectively activate certain tools is to provide the barrel with a single active position, in which the manipulator controlled by the user provides a common user interface with functional control over a single one of the plurality of biopsy tips, e.g., extension and retraction of the sheath, and extension, retraction and rotation of the guidewire. As discussed above, a function for articulation of the sheath by tension on another actuation filament may also be provided. The remaining biopsy tools in the barrel may remain restrained in their undeployed positions, e.g., clamped in position.

Because the barrel has a larger diameter than the sheath, the barrel is maintained outside of the orifice, and a mechanism for engaging and disengaging each respective biopsy tool is also outside the orifice, which, for example, may rotate into position to release one tool while locking the others in retracted position. Thus, a relatively large barrel, e.g., 8-20 mm, may be provided with 2-12 biopsy tools in reserve. The end of the barrel mechanism advantageously serves as the skirt, to limit insertion distance of the sheath into the organ, and provide a well-defined positional reference.

According to a one embodiment, each biopsy tool in the device is separate, with no changeover in control. Thus, for a biopsy device with four deployable biopsy tools, there are four separate concurrently available sheaths with respective guidewires extending from the cartridge. This permits a physician to select the appropriate biopsy tools for a respective procedure, from generic or custom designs. The unused tools remain outside of the organ, while an active tool is in use. In some cases, multiple tools may be advanced into the organ, for example where an endoscope is provided as one of the available tools, and not linked to a particular or single biopsy tool.

On the other hand, in a second embodiment, a mechanism may be provided to mechanically separately engage the sheath, guidewire, and articulation wire for each separate biopsy tool, with a single control system extending from the cartridge. For example, a multi-way clamp, bayonet socket, quick-release, or magnetic mechanism may be provided to individually engage the respective biopsy tool in the active position. The cartridge is typically round, and centered at the orifice during the procedure, so that the non-deployed biopsy devices are eccentric within the cartridge when not in use. As they are brought into the active position, such as by rotation of a lockout/clamp control, and centering, the controls for that respective biopsy tool are also connected and made active. The camera may also be attached to the active biopsy tool at this time. Alternately, the camera is inserted in advance of the biopsy tool, and is separately positioned from the biopsy tools.

In some cases, an electrical mechanism may be provided in the cartridge, for example to latch the mechanical controls, extend the sheath to a desire depth of insertion, rotate the brush, and retract the sheath and/or biopsy brush into the sheath. Typically, the extension of the biopsy brush and axial manipulation are user controlled, and not automated, though a completely automated biopsy is possible.

It is preferred that each biopsy tool have a mechanical limiter to control and constrain the movements within a predetermined range, wherein the predetermined range may differ for the various biopsy tools depending on their intended use of application. Advantageously, axial control limits are referenced to the exterior surface surrounding the orifice of insertion, and the end of the barrel, a ring or protrusion surrounding the barrel, used to maintain this position reference without slipping into the orifice.

For example, the endocervical brush will typically have the sheath extend 0-2 cm past the orifice, and an endometrial brush will typically have the sheath extend 2-10 cm past the cervix, into the uterus, and a brush biopsy tool will extend 1-3 cm beyond the end of the sheath. The endocervical and endometrial brushes may be provided with or without suction, which may be provided by mechanical action of a plunger as the guidewire controlling the brush is withdrawn into the sheath, or by a vacuum provided through the sheath from the cartridge or beyond.

A puncher or cup biopsy tool are typically used under visual observation with the video imager, and may be less mechanically constrained in this circumstance, since the user is presumed to have control over the device during use.

Therefore, the present design permits multiple biopsies to be taken in a single session, from different regions of the organ, and maintained segregated from each other. From a patient perspective, this is advantageous, because the sampling procedure is facilitated, and the combined time and economic burden will typically be less than if separate biopsy tools are employed. Further, compatibility with a single imager used for a plurality of biopsy procedures is also efficient. Finally, in the case of a cartridge that disconnects from a standard handle, the cartridge provides an efficient way to organize and label the samples from a single patient, and makes pathological examination of the various samples from the same patient and same organ more efficient. Finally, because each sample is accurately depth labelled with respect to the orifice, clinically important information is obtained, as compared to traditional biopsy tools which do not provide an accurate depth reference. It is noted that a memory card, such as a micro-SD card, may be associated with the cartridge, which includes video and/or manipulation history information for each biopsy tool, which is automatically recorded and maintained, and which may be readily passed to the pathologist or made part of the patient's record.

It is therefore an object to provide a tissue sampling device, comprising: a flexible sheath having at least a distal portion configured to maintain an internal vacuum; a skirt stopper configured to maintain the sheath at a fixed insertion depth through the cervix within the uterus; and a displaceable structure within the sheath, to form a coaxial structure; the displaceable structure having a first end extending from a proximal end of the sheath and second end configured to, in a first state, extend from a distal end of the sheath, and in a second state, to be retracted into the distal end of the sheath; the second end of the displaceable structure having a cellular sampling structure, preceded by a suction element; and the coaxial structure being configured such that a tension on the first end of the displaceable structure at the proximal end of the sheath results in a retraction of the displaceable structure from the first state to the second state, to generate the suction to cause a displacement of media external to the sheath into the sheath distal to the piston.

The displaceable structure may terminate at the second end in an atraumatic bulb.

The cellular sampling structure may comprise a brush.

The brush may comprise a plurality of bristles extending radially from the displaceable structure. The brush may have a cross section which tapers with respect distance from the second end. The brush may have a helical cross sectional profile.

The coaxial structure may be configured for insertion to a predetermined depth into the cervical os of a uterus of a human, to retrieve an endometrial biopsy sample, and to be withdrawn from the cervical os of the uterus.

The coaxial structure may be further configured to be: inserted into the cervical os with the displaceable structure in the second state to a predetermined depth; extended into the first state with the cellular sampling structure within the uterus; manipulated by a user by movement of the first end of the displaceable structure to dislodge cells within the uterus; retracted into the second state within the uterus, to cause the vacuum to withdraw a liquid sample surrounding the cellular sampling structure in to the distal end of the sheath; and retracted from the cervical os with the displaceable structure in the second state.

The displaceable structure may comprise a spirally twisted flexible guidewire.

The sheath may have an outer diameter of between 1 and 3 mm and a length between 20 and 50 cm.

It is also an object to provide a tissue sampling method, comprising: providing a coaxial structure, comprising a flexible sheath having at least a distal portion configured to maintain an internal vacuum, a skirt around the flexible sheath, configured to limit an insertion depth of the flexible sheath into a human cervix; and a displaceable structure within the sheath, to form a coaxial structure, the displaceable structure having a first end extending from a proximal end of the sheath and second end configured to, in a first state, extend from a distal end of the sheath, and in a second state, to be retracted into the distal end of the sheath, and the second end of the displaceable structure having a cellular sampling structure, preceded by a piston; and applying a tension on the first end of the displaceable structure at the proximal end of the sheath to case retraction of the displaceable structure from the first state to the second state, generating the vacuum.

The coaxial structure may be configured for insertion into the cervical os of uterus of a human to the predetermined insertion depth, to retrieve an endometrial biopsy sample, and to be withdrawn from the cervical os of the uterus.

The method may, further comprise: inserting the distal portion of the coaxial structure into the cervical os of a uterus, with the displaceable structure in the second state to the predetermined depth; extending the distal portion of the coaxial structure into the first state with the cellular sampling structure within the uterus; manipulating the first end of the displaceable structure to dislodge cells within the uterus; retracting the coaxial structure into the second state within the uterus, to cause the vacuum to withdraw a liquid sample surrounding the cellular sampling structure in to the distal end of the sheath; and retracting the distal portion of the coaxial structure from the cervical os with the displaceable structure in the second state.

The cellular sampling structure may comprise a brush having a plurality of radially extending bristles from the displaceable structure and terminating in an atraumatic bulb.

The displaceable structure may comprise a spirally twisted flexible guidewire, further comprising twisting the guidewire to rotate the cellular sampling structure.

It is a still further object to provide a flexible coaxial biopsy device, comprising: a tubular sheath having a wall configured to maintain an internal vacuum with respect to an exterior of the tubular sheath; a flanged element on an outer surface of the tubular sheath, configured to limit a depth of insertion of the tubular sheath into a cervix; a displaceable wire within the tubular sheath; and a cellular sampling device configured to disrupt a surface of a tissue, mounted on the displaceable structure distal to the element, configured to protrude from a distal end of the tubular sheath when the displaceable element is disposed in a first state, and to be contained within the distal end of the tubular sheath when the displaceable element is disposed in a second state.

The cellular sampling device may comprise a plurality of bristles extending outwards from the displaceable wire, terminating at the distal end in an atraumatic bulb.

The device may be configured for insertion into the cervical os of a uterus of a human to the predetermined depth, to retrieve an endometrial biopsy sample from inside the uterus, and to be withdrawn from the cervical os of the uterus after the endometrial biopsy sample is obtained.

The device may be further configured to be: inserted into the cervical os with the displaceable wire in the second state to the predetermined depth; extended into the first state with the cellular sampling device within the uterus; manipulated by movement of the first end of the displaceable wire to dislodge endometrial cells; retracted into the second state within the uterus, to draw the vacuum to withdraw a liquid sample surrounding the cellular sampling device in to the distal end of the tubular sheath; and retracted from the cervical os with the displaceable wire in the second state.

The device may further comprise an element that creates a negative pressure within the tubular sheath when the displaceable wire is withdrawn into the tubular sheath.

The biopsy brush described above may also be revised for use as an anal biopsy brush, and an endometrial biopsy brush and anal biopsy brush may be provided together as a kit, optionally alone with a vial of preservative solution (for a single brush), or a plurality of vials of preservative for a kit. The kit is preferably a sterile package, which may be double wrapped, containing the biopsy brush or bushes, a vial or vials of preservative, and optionally an acceptable lubricant for cytological sampling, and optionally a disposable sterile sheet or drape.

The anal biopsy brush differs from an intrauterine biopsy brush in that it will be shorter, since the working distance between the physician or caregiver and patient orifice is less. The, for intrauterine use, the sheath is typically 20-25 cm long, with a 4 cm long brush and 2 cm exposed guidewire, such that the wire is 26-31 cm long, past the end of the handle to which it is bound, with a skirt on the sheath about 4 cm from the distal end.

An anal biopsy brush sheath will typically be 8-12 cm long, with the skirt about 4 cm from the distal end. For example, an anal biopsy brush may have a sheath 8 cm long with the skirt located 4 cm from the distal end, having a guidewire 14-18 cm long for sampling in the rectum up to 6 cm past the end of the sheath.

A kit may therefore include a long intrauterine biopsy device having a sheath length of about 20 cm, a short anal biopsy device having a sheath length of about 8 cm, two vials of cytological preservative, a packet of water-based cytologically acceptable lubricant (e.g., Surgilube®, which preferably does not include carbomers), a sterile drape, and package insert labelling instructions (which may be imprinted on the packaging as appropriate). Any lubricant should be applied on the exterior of the sheath, between the skirt or flange and distal tip, with the brush in the retracted position, with care taken to avoid getting lubricant on the end of the sheath or brush.

BRIEF DESCRIPTION OF THE DRAWINGS

FIGS. 1A, 1B, 2A and 2B, show a prior art Tao Brush s in the extended and retracted state with respect to the sheath, respectively, the inner obturator and disrupting elements, which may be, for example, a brush, tapered helical screw, loop or loop with brush elements, or the like;

FIGS. 4A and 4B show a Pipelle endometrial biopsy device of the prior art, in the extended and retracted states, respectively.

FIGS. 5A-5C shows use of Pipelle device in a biopsy procedure.

DETAILED DESCRIPTION OF THE PREFERRED EMBODIMENTS

Example 1

Figure 1A:
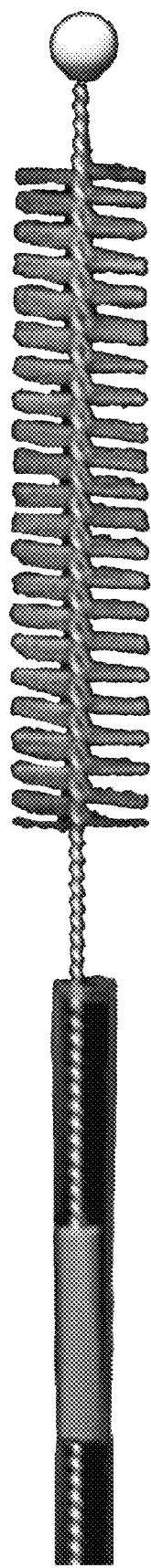
Figure 1B:
Figure 2A:
Figure 2B:
Figure 3C:
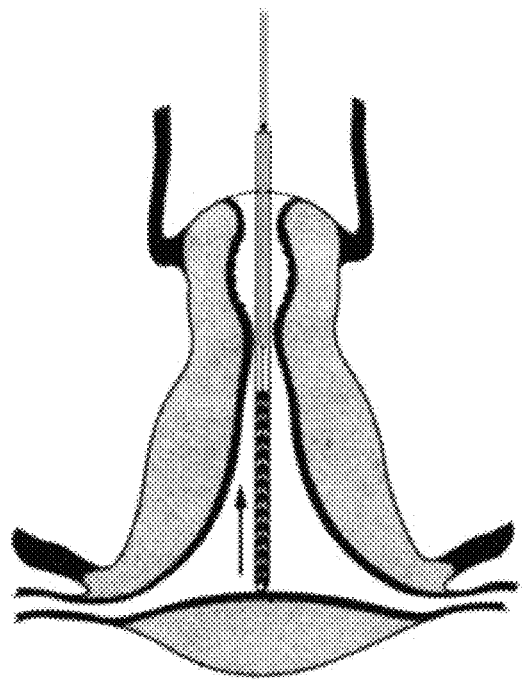
FIGS. 3A-3D show illustrations of use of the Tao Brush™.
Figure 3D:
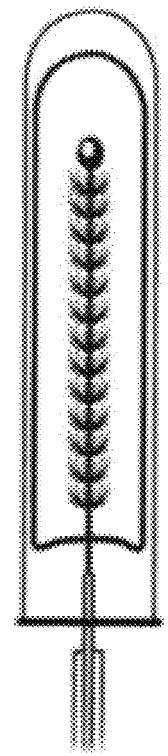
Figure 3A:
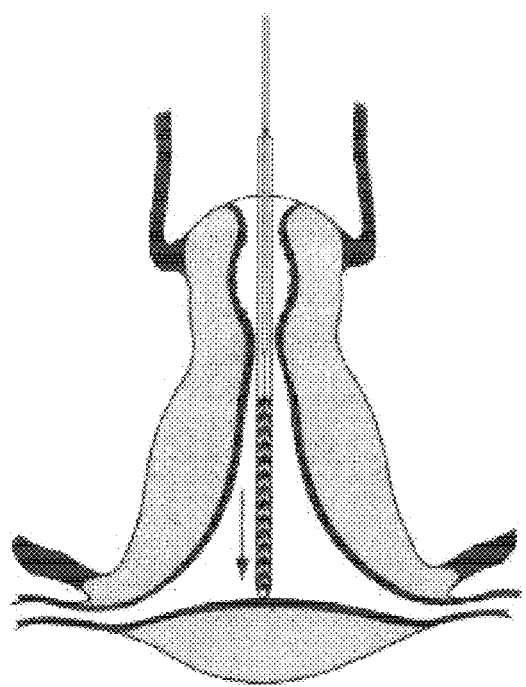
Figure 3B:
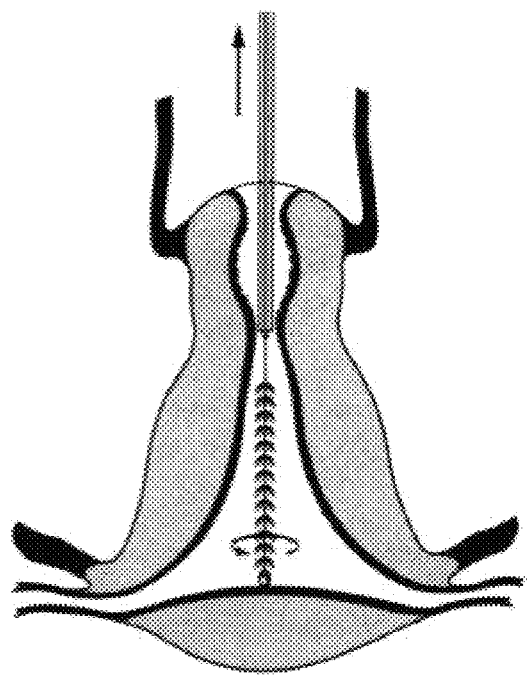
Figure 6:
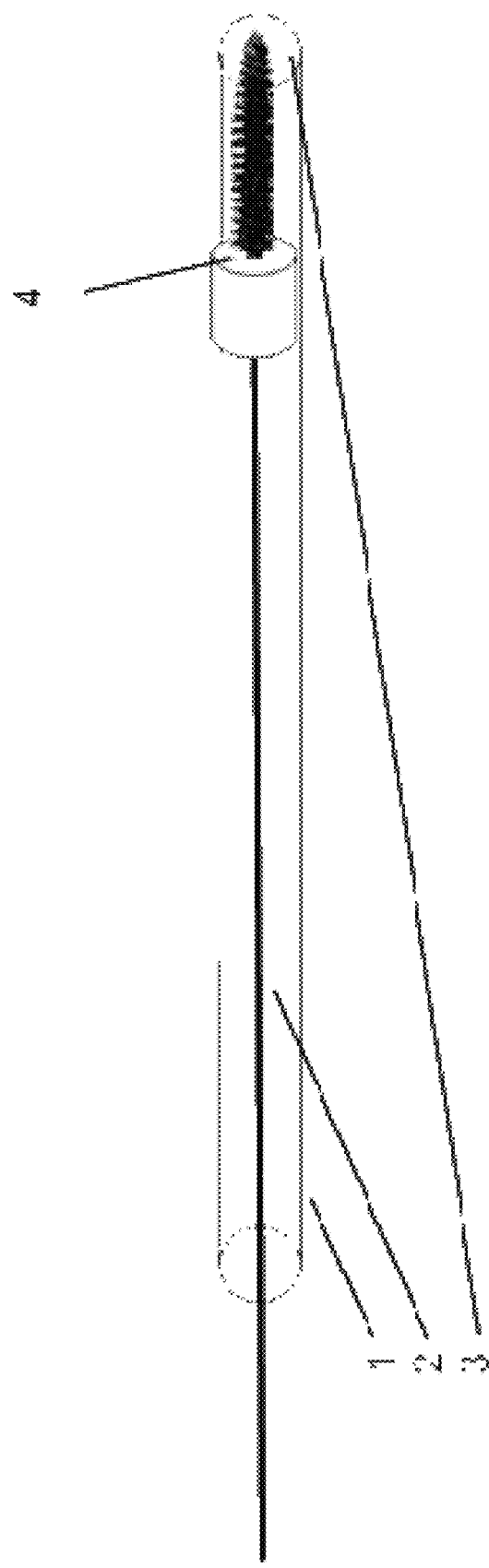
FIGS. 6 and 7 show an improved endometrial biopsy brush with suction, according to U.S. Pat. Nos. 9,351,712, 8,920,336, 8,517,956, and 8,348,856.
Figure 7:
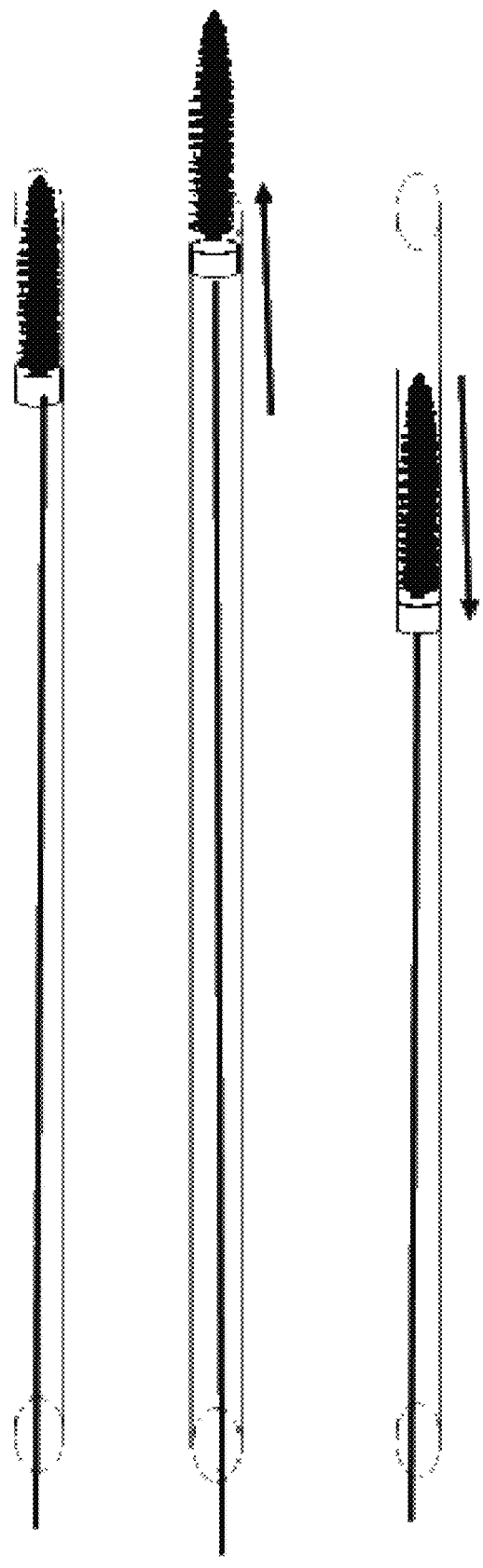
Figure 8:
FIG. 8 shows a guidewire and biopsy brush according to the present invention.

A preferred embodiment of the present invention consists of an intrauterine biopsy device having an outer thin walled tube of approximately 2.25 mm outside diameter and 1.2 mm inside diameter; length is between 20-50 cm, e.g., 22 cm. This tube may be a clear, bendable but self-supporting plastic tube, made e.g., of nylon. The guidewire is preferably a twisted stainless steel wire of approximately 0.1-0.2 mm diameter, having sufficient mechanical properties to convey the forces for extension and retraction of the brush during use. At the distal end of the guidewire is a biopsy brush, shown in FIGS. 8 and 11, tipped with an atraumatic bulb. The brush may be about 4 cm long, and extend about 2 cm past the end of the sheath when extended. The O-ring preferably remains within the sheath over the entire range of travel, to avoid problems re-engaging the end of the sheath. For example, the O-ring (or more generally, plunger attached to the wire) may be, for example, 2-5 mm from the end of the sheath when extended.

An anal biopsy device may also be provided, having an outer thin walled tube of approximately 2.25 mm outside diameter and 1.2 mm inside diameter; length is between 8-12, e.g., 8 cm. This tube may be a clear, bendable but self-supporting plastic tube, made e.g., of nylon. The guidewire is preferably a twisted stainless steel wire of approximately 0.1-0.2 mm diameter, having sufficient mechanical properties to convey the forces for extension and retraction of the brush during use. At the distal end of the guidewire is a biopsy brush, shown in FIGS. 8 and 11, tipped with an atraumatic bulb. The brush for the anal biopsy device may also be 4 cm long, with the O-ring or plunger 2-5 mm from the end of the sheath when the brush is extended.

The wire may be periodically marked, such as in 1 cm increments, so that the physician or biopsy device operator can estimate the brush insertion with respect to the proximal end of the sheath.

At one end, the one that enters the uterus or anus, the biopsy brush is formed. A tight fitting O-ring around the guidewire, shown in FIG. 11, acts as a piston and creates the suction as the obturator is withdrawn through the outer thin walled tube.

In another embodiment, the O-ring may be disposed about 2.5 cm from the tip, with the brush extending about 1.5 cm from the tip, with 1 cm of bare wire between them.

Figure 9:
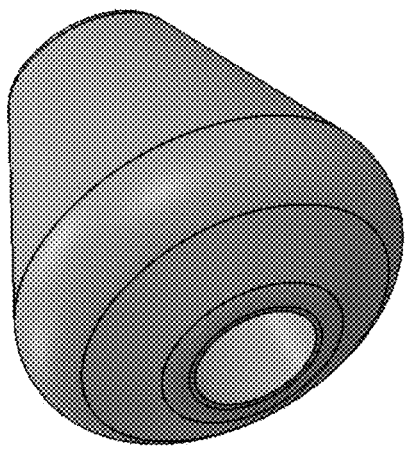
FIG. 9 shows a shirt stopper according to the present invention.
Figure 10:
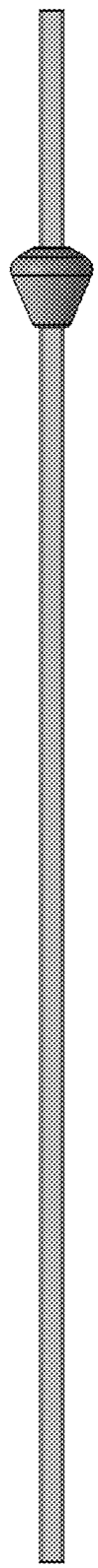
FIG. 10 shows a narrow sheath with skirt stopper installed according to the present invention.
Figure 11:
FIG. 11 shows a complete biopsy device with manual handle, skirt stopper, sheath, guidewire, brush, and O-ring, according to the present invention.

As shown in FIGS. 9, 10 and 11, a skirt stopper is provided about the exterior of the thin walled tube, near the distal end, which may be in fixed position or manually slidable. The skirt is approximately 1 cm in diameter, and may be formed of nylon, polyurethane, silicone, neoprene, or other medically acceptable plastic or rubber. Typically, the skirt is fixed in position, and may be glued (e.g., UV activated methyl-methacrylate adhesive) or molded to the sheath in position.

The biopsy device is use as follows:

The brush is retracted completely into the outer sheath.

The sheath is inserted, through the vagina, into the cervix, until the skirt stopper meets the external os of the cervix. The tip of the brush should be displaced from the fundus.

The outer sheath is pulled back until it stops, i.e., abuts the handle. The brush is then rotated by holding the sheath still and turning the handle. For example, the brush may be rotated in a clockwise manner until a reference mark on the handle indicates completion of a 360° turn, and then rotated counterclockwise until the reference mark on the handle indicates completion of a−360° turn. Alternately, the brush may be rotated in only one direction by completing 4 or 5 360° rotations. In some cases, the brush may be repositioned axially, though it should not be withdrawn into the sheath until the sampling is completed.

After sampling with the brush, the guidewire is pulled at the handle, until the sheath hits the stop (e.g., the edge of the handle), thereby suctioning fluid surrounding the tip into the sheath, and then withdrawing the brush into the sheath.

After withdrawal of the device from the vagina, the brush and fluids in the sheath are immersed in a cytology preservative, such as formalin, and the sample is washed from the brush into the preservative by moving the brush in and out of the sheath immersed in the fluid.

The invention may be used, for example, to sample the inside of the uterus to diagnose abnormalities. It can detect or exclude a cancer. It can obtain an adequate tissue sample to determine infertility causes.

The anal brush is similarly employed. Such a biopsy tool typically has a shorter sheath and guidewire than an endocervical brush biopsy tool, because of the easier anatomical access. For example, the sheath may be 10-15 cm long, and the brush may extend 2-6 cm beyond the end of the sheath. As with the endocervical brush biopsy tool described above, a skirt is preferably provided which prevents insertion of the sheath into the anus beyond the sheath, to provide a physical reference distance for insertion. In some cases, the skirt may be repositioned on the sheath, to permit the physician the ability to determine at what depth of insertion the sample should be acquired. Advantageously, the readjustment requires more force than would be available by applying an unconstrained compression of the sheath against the skirt stopper, so that the position is maintained during use, but the stiction force can be overcome when the biopsy tool is external to the body.

Example 2

According to a second embodiment, a multiple sample biopsy device is provided, capable of obtaining and segregating a plurality of biopsy samples taken in a single session. This therefore requires a plurality of biopsy brushes or tools, and a plurality of sheaths in which the tools are extended and retracted.

As discussed above, a depth of insertion positional reference, such as a skirt stopper may be provided. However, where the multiple biopsy tool system has a mechanism maintained outside of the orifice, the diameter of the tool may be sufficiently large to act as the stopper without additional structures.

According to one design, each biopsy tools is separate, including a sheath and guidewire control. A set of biopsy tools are aggregated in an outer tube housing. The tube has a conical internal profile at the distal end, so that a single biopsy tool may be advanced past the end of the housing, into the orifice or canal from which a biopsy is to be taken. In some cases, endoscopic guidance of the biopsy is desired, and in that case, a second sheath which supports the endoscope and lighting may be advanced as well. He endoscope sheath may also inject saline for visualization, though in the case of a brush biopsy, this is disfavored, since the saline will wash away the dislodged cells, and reduce the positional accuracy of sampling. An inert gas, such as $CO_2$ may also be injected through the sheath, in known manner.

For example, the biopsy brush may be provided in a 3 mm tube, with 6 separate brushes provided within a housing. A stop may be provided at the proximal end of each sheath within the housing, to prevent over-withdrawal. Markings may be provided on each sheath, to inform the physician about the depth of insertion. In some cases, the physician may intend gradated sampling at a series of depths in the orifice, and advantageously, each respective sheath may have a stopper which limits its depth of insertion, and provides the physician with haptic feedback when that depth is achieved. This stopper may be a simple O-ring or clamp, which is adjusted by the physician for each biopsy sampling tool, before the procedure. The guidewire for each sampling tool may also have depth limits. Of course, the retracted position with the biopsy tool fully withdrawn into the sheath represents one extreme, and a clamp or limit may be provided on the manipulation end to control how far the guidewire may be extended beyond the end of the sheath.

In this first design, each biopsy brush may be of known type, with the optional addition of the insertion and retraction limiters, and indeed, the housing for arranging a multiple biopsy sample session may itself may be provided independent of the biopsy brushes.

In general, the housing avoids the need for a separate skirt stopper, though the housing may terminate in a skirt stopper.

Example 3

According to a second design of the multiple sample biopsy device, a single manipulator extends from a housing, which itself contains a plurality of biopsy tools.

As discussed above, a depth of insertion positional reference, such as a skirt stopper may be provided. However, where the multiple biopsy tool system has a mechanism maintained outside of the orifice, the diameter of the tool may be sufficiently large to act as the stopper without additional structures.

Thus, a selectively engageable coupling is provided between a single guidewire and the various tools. The coupling thus links the guidewire, that extends to a physician manipulation interface, such as a grasping element, a handle, or a pivotal mechanism, to the individual guidewire for each tool. Advantageously, the plurality of tools are provide in a rotating barrel, which serves as the housing. Each biopsy tool, when engaged with the manipulation guidewire, can be advanced with its respective sheath an insertion distance, and then the biopsy head advanced beyond the sheath, and twisted or otherwise manipulated to obtain a biopsy sample. The biopsy head is then withdrawn back into the sheath, the sheath with biopsy head covers then withdrawn back into the cartridge, and the barrel twisted so another biopsy tool may then be engaged.

Therefore, the coupling is a coaxial coupling, which separately links and controls the sheath and the guidewire within each respective sheath. For example, within the cartridge, the end of the sheath may terminate in a steel ring, which is magnetically permeable. Thus, a magnetic coupling can be used to connect and disconnect the sheaths. Further, the inactive biopsy tools may also be held in place by another magnet, which is typically an electromagnet, or a permanent magnet with an electromagnetic release. The guidewire may be selectively connected to the external manipulation guidewire with a spring-loaded clamp. As the barrel is turned, the spring loaded clamp releases, and re-engages as it reaches the next detent position with the next biopsy tool aligned with the spring clamp. Within the barrel, the guidewire from the biopsy tool extends beyond the proximal end of the respective sheath.

The barrel is typically at least as long as the desired depth of insertion of the sheath into the patient. Thus, if it is desired to have a 12 cm depth of insertion, the barrel mechanism may be 13-16 cm long.

Figure 12:
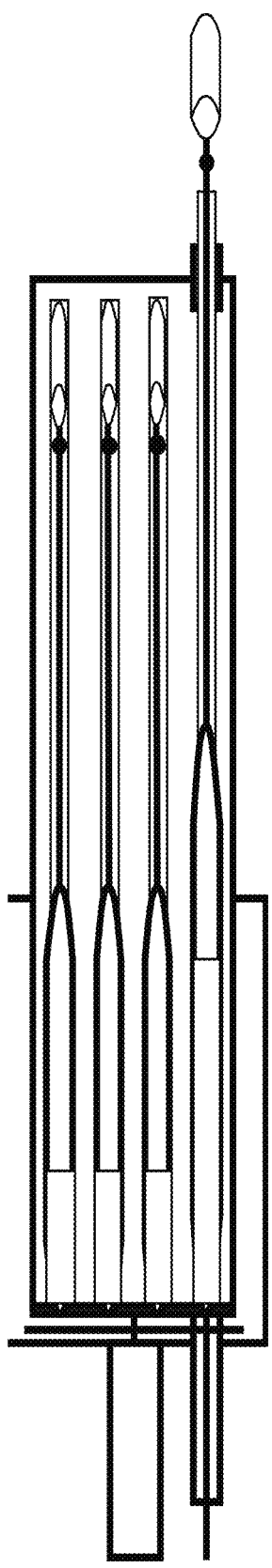
FIG. 12 shows an arrangement of an independently controllable, biopsy multiple sample, biopsy device showing four similar biopsy sampling tools.
Figure 13:
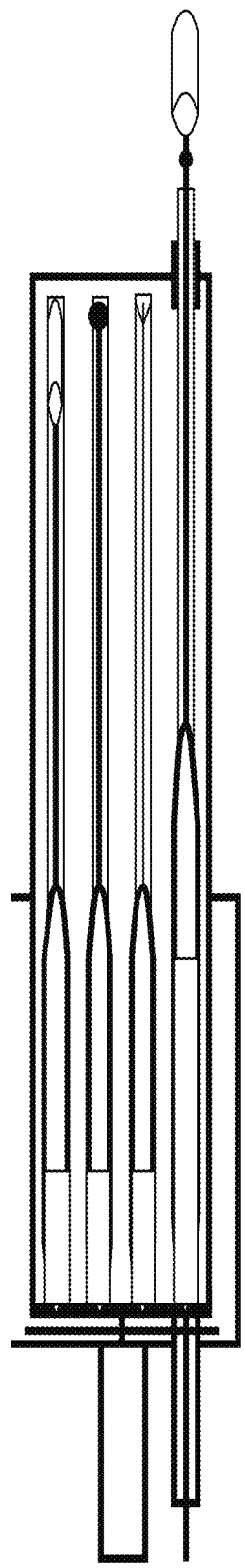
FIG. 13 shows an arrangement of an independently controllable, biopsy multiple sample, biopsy device showing four different biopsy sampling tools.

As shown in FIG. 12, a plurality of similar brushes are provided in a cartridge. In FIG. 13 a plurality of different brushes are provided in the cartridge. The cartridge has an exit port for the engaged biopsy tool. Each brush has its own associated sheath, which may be independently advanced into the patient, depending on which tool is engaged. A mechanism at the proximal end of the housing controls the selection of the barrel position by an angle of rotation, the latching of the sheath of the respective active tool to the tool advancement control, the clamping of the guidewire of the respective active tool to the guidewire control for manipulation by the physician, and in some cases, other controls, such as deflection angle of the sheath.

Figure 14:
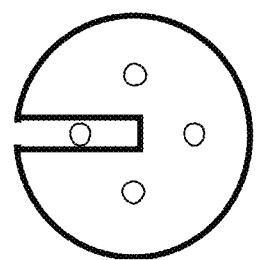
FIG. 14 shows a detail of a selector which permits manipulation of a single biopsy sampling tool in a barrel cartridge.

FIG. 14 shows an end view of a portion of the mechanism in the barrel, wherein one guidewire is free to be manipulated by the physician, while access for manipulation of the other guidewires is locked out.

FIG. 12 shows a bulb provided just proximal to each sampling brush, which is provided to draw a sampling vacuum when the respective brush is withdrawn back into the sheath.

In FIG. 13, only one biopsy tool has such a feature. The biopsy sampling tools, may be, for example, an endocervical sampler, an endometrial sampler, a punch sampler, and an endometrial sampler with suction.

In some cases, the sheath itself may be articulable or angularly guidable to direct the biopsy tool to a desired region. The articulable sheath may be a single axis, i.e., a curvature of the end of the sheath, typically as a result of a tension on a tensile element such as cable, guidewire or filament attached to the wall of the sheath, not shown in in the figures . . . . By controlling the angle of curvature, and the rotational angle of the sheath with respect to the organ, a reasonable range of control is provided. Similarly, a punch, or snare, or encapsulating biopsy device may also be controlled by a tension, which may be a wire or polymer filament. Thus, the case of a single guidewire with a single degree of freedom (advance/retract) is a simplest case, and additional controls and degrees of freedom may be provided. The controls for these tools may also be selectively engaged through a mechanism, or provided individually to the user.

An endoscopic imager (not shown in the figures) may be provided, preferably as a feature of the housing, so that it may be used with various biopsy tools within the housing. For example, a 1-3 mm endoscopic camera with fiber optic lighting, may be provided, e.g., the On Semiconductor OVM6946¹⁄₁₈" 400×400 imager.

What is claimed is:

1. An endometrial tissue sampling device, comprising:
   (a) a coaxial structure comprising:
      a flexible sheath having a proximal end and a distal end, having a wall configured to maintain an internal vacuum;
      a flexible tensile displaceable structure within the flexible sheath, having a first end extending beyond the proximal end of the sheath and a second end configured to, in a first state, extend beyond the distal end of the flexible sheath, and in a second state, to be retracted into the distal end of the flexible sheath;
      a cellular sampling structure at the second end; and
      a piston, preceding the cellular sampling structure, riding against an inner wall of the flexible sheath and being configured to draw an internal vacuum in the flexible sheath with respect to the second end by a retraction of the flexible tensile displaceable structure from the first state to the second state, and a corresponding retraction of the piston into the flexible sheath to draw media external to the flexible sheath into the flexible sheath distal to the piston; and
   (b) a skirt stopper, comprising an elastomer and having an aperture surrounding the flexible sheath, configured to:
      be repositionable on the flexible sheath by sliding along an outer surface of the flexible sheath under a manual force sufficient to overcome a stiction to a stop position; and
      maintain the flexible sheath at a defined first insertion depth under a compressive force of the sheath against the skirt stopper with the skirt stopper in contact with the cervix during manipulation of the flexible tensile displaceable structure,
      to thereby permit sampling by the cellular sampling structure at the defined insertion depth;
   wherein the coaxial structure is configured to:
      be inserted into the cervix of a human, with the skirt stopper constrained at the stop position external to the external cervical os, and the distal end extending past the internal cervical os,
      retrieve an endometrial biopsy sample comprising cells and aspirate drawn by the internal vacuum, by extension of the flexible tensile displaceable structure and cellular sampling structure past the distal end and subsequent retraction within the distal end, and
      be withdrawn from the uterus with the cellular sampling structure contained within the flexible sheath protected from sampling from unintended areas.

2. The tissue sampling device according to claim 1, wherein the flexible tensile displaceable structure terminates at the second end in an atraumatic bulb.

3. The tissue sampling device according to claim 1, wherein the cellular sampling structure comprises a brush.

4. The tissue sampling device according to claim 3, wherein the brush comprises a plurality of bristles extending radially from the flexible tensile displaceable structure.

5. The tissue sampling device according to claim 3, wherein the brush has a cross section which tapers with respect to distance from the second end.

6. The tissue sampling device according to claim 3, wherein the brush has a helical cross sectional profile.

7. The tissue sampling device according to claim 1, wherein the coaxial structure is further configured to be:
  inserted into the external cervical os with the flexible tensile displaceable structure in the second state to the defined first insertion depth, and the skirt stopper abutting the cervix;
  extended into the first state with the cellular sampling structure past the internal cervical os within the uterus proximate to the endometrium;
  manipulated by a user by axial and rotational movement of the first end of the flexible tensile displaceable structure to dislodge endometrial cells;
  retracted into the second state within the uterus, to cause the displacement of the piston against the inner wall of the sheath to draw the internal vacuum and to withdraw a liquid sample surrounding the cellular sampling structure into the distal end of the flexible sheath; and
  retracted from the external cervical os with the flexible tensile displaceable structure in the second state.

8. The tissue sampling device according to claim 1, wherein the flexible tensile displaceable structure comprises a spirally twisted flexible guidewire.

9. The tissue sampling device according to claim 1, wherein the flexible sheath has an outer diameter of between 1 and 3 mm and a length between 20 and 50 cm.

10. The tissue sampling device according to claim 1, wherein the skirt stopper comprises a flanged element on an outer surface of the flexible sheath adapted to be inserted through a human vagina to abut the cervix, and the flexible sheath is configured for insertion into the internal cervical os of the uterus to the defined first insertion depth, to retrieve an endometrial biopsy sample from inside the uterus, and to be withdrawn from the external cervical os of the uterus after the endometrial biopsy sample is obtained at the second insertion depth,
  the tissue sampling device being further configured to be:
    inserted into the cervical os with the displaceable wire in the second state to the defined first insertion depth;
    extended into the first state with the cellular sampling device within the uterus;
    manipulated by axial and rotational movement of the first end of the flexible tensile displaceable structure to dislodge endometrial cells;
    retracted into the second state within the uterus, to draw the internal vacuum to withdraw a liquid sample surrounding the cellular sampling device in to the distal end of the flexible sheath; and
    retracted from the external cervical os with the displaceable wire in the second state.

11. The tissue sampling device according to claim 1, comprising:
  a plurality of flexible sheaths, each respective flexible sheath having a respective proximal end and a respective distal end, and a respective wall configured to maintain an internal vacuum, a respective flexible tensile displaceable structure within each respective flexible sheath, and a respective cellular sampling structure, the plurality of flexible sheaths and respective tensile displaceable structures forming a plurality of coaxial structures; and
  a housing, configured to selectively engage each respective flexible tensile displaceable structure of each respective coaxial structure to a user interface, such that when selectively engaged, tension and compression are passed from the user interface to the respective flexible tensile displaceable structure to transition the respective flexible tensile displaceable structure between the first state and the second state, and when selectively disengaged, tension and compression are not passed from the user interface to the respective flexible tensile displaceable structure.

12. The tissue sampling device according to claim 11, wherein the plurality of flexible sheaths are respectively associated with at least two different physical configurations of cellular sampling structures.

13. The tissue sampling device according to claim 1, wherein:
  the stiction retains the skirt stopper in position on the outer surface of the flexible sheath against an unconstrained compression of the sheath against the skirt stopper during the retrieval of the endometrial biopsy sample.

14. A multiple-sample biopsy device, comprising:
  a plurality of concurrently available flexible sheaths;
  a plurality of flexible displaceable structures, each respective flexible displaceable structure being within a respective concurrently available flexible sheath, to form a coaxial structure with the respective concurrently available flexible sheath;
  each flexible displaceable structure having a first end extending from a proximal end of the respective concurrently available flexible sheath and second end configured to, in a first state, extend from a distal end of the respective concurrently available flexible sheath, and in a second state, to be retracted into the distal end of the respective concurrently available flexible sheath;
  the second end of each respective flexible displaceable structure having a cellular sampling structure; and
  a housing, configured to selectively individually engage with any single respective flexible displaceable structure within one of the plurality of concurrently available flexible sheaths to a user interface, such that when engaged, tension and compression are passed from the user interface to the single respective flexible displaceable structure to transition the single respective flexible displaceable structure between the first state and the second state, and when disengaged, tension and compression are not passed from the user interface to the single respective flexible displaceable structure.

15. A tissue sampling method, comprising:
  providing an endometrial tissue sampling device comprising:
  (a) a coaxial structure comprising:
    a flexible sheath having a proximal end and a distal end, having an outer surface and a wall configured to maintain an internal vacuum;
    a flexible tensile displaceable structure within the flexible sheath, having a first end extending beyond the proximal end of the sheath and a second end configured to, in a first state, extend beyond the distal end of the flexible sheath, and in a second state, to be retracted into the distal end of the flexible sheath;
    a cellular sampling structure at the second end; and
    a piston, preceding the cellular sampling structure, riding against an inner wall of the flexible sheath and being configured to draw an internal vacuum in the flexible sheath with respect to the second end by a retraction of the flexible tensile displaceable structure from the first state to the second state, and a corresponding retraction of the piston into the flexible sheath to draw media external to the flexible sheath into the flexible sheath distal to the piston; and (b) a skirt stopper, comprising an elastomer and having an aperture surrounding the flexible sheath, configured to:
  be repositionable on the flexible sheath by sliding along an outer surface of the flexible sheath under a manual force sufficient to overcome a stiction to a stop position; and
  maintain the flexible sheath at a defined first insertion depth under a compressive force of the sheath against the skirt stopper with the skirt stopper in contact with the cervix during manipulation of the flexible tensile displaceable structure,
  to thereby permit sampling by the cellular sampling structure at the defined insertion depth;
wherein the coaxial structure is configured to:
  be inserted into the cervix of a human, with the skirt stopper constrained at the stop position external to the external cervical os, and the distal end extending past the internal cervical os,
  retrieve an endometrial biopsy sample comprising cells and aspirate drawn by the internal vacuum, by extension of the flexible tensile displaceable structure and cellular sampling structure past the distal end and subsequent retraction within the distal end, and
  be withdrawn from the uterus with the cellular sampling structure contained within the flexible sheath protected from sampling from unintended areas;
inserting the distal into the external cervical os with the flexible tensile displaceable structure in the second state to the defined first insertion depth, so that the skirt stopper abuts the cervix;
repositioning the skirt stopper to the stop position by sliding along the outer surface of the flexible sheath under the manual force sufficient to overcome the stiction from compression of the sheath against the skirt stopper;
manipulating the flexible tensile displaceable structure to cause axial and rotational movement of the cellular sampling structure against the endometrium and dislodge endometrial cells, while maintaining the flexible sheath at the defined first insertion depth with the skirt stopper in contact with the cervix;
applying a tension on the first end of the flexible tensile displaceable structure at the proximal end of the flexible sheath to cause retraction of the flexible tensile displaceable structure from the first state to the second state, generating the vacuum by a withdrawal of the piston sliding against an inner wall of the flexible sheath; and
withdrawing the coaxial structure from the external cervical os of the uterus.

16. The method according to claim 15, further comprising:
  extending the distal end of the coaxial structure into the first state with the cellular sampling structure within the human uterus; and
  retracting the distal end of the coaxial structure from the external cervical os with the flexible tensile displaceable structure in the second state.

17. The method according to claim 15, wherein the cellular sampling structure comprises a brush having a plurality of radially extending bristles from the flexible tensile displaceable structure and terminating in an atraumatic bulb.

18. The method according to claim 15, wherein the flexible tensile displaceable structure comprises a spirally twisted flexible guidewire, further comprising twisting the guidewire to rotate the cellular sampling structure.

19. The method according to claim 15, wherein a plurality of independently controllable coaxial structures are provided, with a common user interface, and a mechanism which ensures that the common user interface controls a transition between the first state and the second state of only a single coaxial structure at any respective time.

20. The method according to claim 15, further comprising:
  retaining the skirt stopper in the stop position against an unconstrained compression of the sheath against the skirt stopper during said manipulating of the flexible tensile displaceable structure.

* * * * *